United States Patent
Trzasko et al.

(10) Patent No.: US 12,085,631 B2
(45) Date of Patent: Sep. 10, 2024

(54) MODEL-BASED ITERATIVE RECONSTRUCTION FOR MAGNETIC RESONANCE IMAGING WITH ECHO PLANAR READOUT

(71) Applicant: Mayo Foundation for Medical Education and Research, Rochester, MN (US)

(72) Inventors: Joshua D. Trzasko, Rochester, MN (US); Matthew A. Bernstein, Rochester, MN (US); Uten Yarach, Rochester, MN (US)

(73) Assignee: May Foundation for Medical Education and Research, Rochester, MN (US)

( * ) Notice: Subject to any disclaimer, the term of this patent is extended or adjusted under 35 U.S.C. 154(b) by 28 days.

(21) Appl. No.: 17/606,645

(22) PCT Filed: Apr. 23, 2020

(86) PCT No.: PCT/US2020/029471
§ 371 (c)(1),
(2) Date: Oct. 26, 2021

(87) PCT Pub. No.: WO2020/219642
PCT Pub. Date: Oct. 29, 2020

(65) Prior Publication Data
US 2022/0236358 A1 Jul. 28, 2022

Related U.S. Application Data

(60) Provisional application No. 62/839,019, filed on Apr. 26, 2019.

(51) Int. Cl.
*G01R 33/561* (2006.01)
*G01R 33/48* (2006.01)
*G01R 33/56* (2006.01)

(52) U.S. Cl.
CPC ..... *G01R 33/5616* (2013.01); *G01R 33/4818* (2013.01); *G01R 33/5608* (2013.01)

(58) Field of Classification Search
CPC ............ G01R 33/4818; G01R 33/5608; G01R 33/5616
See application file for complete search history.

(56) References Cited

U.S. PATENT DOCUMENTS 4,591,789 A 5/1986 Glover et al.
2017/0299680 A1* 10/2017 Ye ...................... G01R 33/5602
(Continued)

OTHER PUBLICATIONS

Yarach, U., In, M.-H., Chatnuntawech, I., Bilgic, B., Godenschweger, F., Mattern, H., Sciarra, A. and Speck, O. (2017), Model-based iterative reconstruction for single-shot EPI at 7T. Magn. Reson. Med, 78: 2250-2264. https://doi.org/10.1002/mrm.26633 (Year: 2017).*
(Continued)

*Primary Examiner* — Gregory H Curran
(74) *Attorney, Agent, or Firm* — Quarles & Brady LLP (57) ABSTRACT

Images are reconstructed from k-space data using a model-based image reconstruction that prospectively and simultaneously accounts for multiple non-idealities in accelerated single-shot-EPI acquisitions. In some implementations, non-linear regularization (e.g., sparsity regularization) is also incorporated to mitigate noise amplification. The reconstructed images have reduced distortions and noise amplification effects relative to those images that are processed using conventional post-reconstruction techniques to correct for non-idealities.

22 Claims, 3 Drawing Sheets

(56) References Cited

U.S. PATENT DOCUMENTS

2017/0307707 A1* 10/2017 Huang ............... G01R 33/5615
2019/0369185 A1* 12/2019 Setsompop ........ G01R 33/4818

OTHER PUBLICATIONS

Tao, S., Trzasko, J.D., Shu, Y., Huston, J., III, Johnson, K.M., Weavers, P.T., Gray, E.M. and Bernstein, M.A. (2015), NonCartesian MR image reconstruction with integrated gradient nonlinearity correction. Med. Phys., 42: 7190-7201. https://doi.org/10.1118/1.4936098 (Year: 2015).*

Lustig, M. and Pauly, J.M. (2010), SPIRiT: Iterative self-consistent parallel imaging reconstruction from arbitrary k-space. Magn. Reson. Med., 64: 457-471. https://doi.org/10.1002/mrm.22428 (Year: 2010).*

Otazo, R., Candès, E. and Sodickson, D.K. (2015), Low-rank plus sparse matrix decomposition for accelerated dynamic MRI with separation of background and dynamic components. Magn. Reson. Med., 73: 1125-1136. https://doi.org/10.1002/mrm.25240 (Year: 2015).*

Andersson, JLR, et al., "How to correct susceptibility distortions in spin-echo echo-planar images: application to diffusion tensor imaging" NeuroImage (2003) 20(2): 870-888.

Ahn, C.B., et al., "Analysis of eddy currents induced artifacts and temporal compensation in nuclear magnetic resonance imaging" Trans Med Imaging (1991) 10: 47-52.

Beck, A., et al., "A fast iterative shrinkage-thresholding algorithm for linear inverse problems" SIAM Journal on Imaging Sciences (2009) 2(1): 183-202.

Fessler, J.A., "Model-based image reconstruction for MRI." IEEE Signal Process Mag (2010) 27:81-89.

Foo, T.K., "Lightweight, compact, and highperformance 3 T MR system for imaging the brain and extremities" MRM (2018) doi: 10.1002/mrm.27175.

Holland, D., et al., "Efficient Correction of Inhomogeneous Static Magnetic Field-Induced Distortion in Echo Planar Imaging" Neuroimage (2010) 50: 175-183.

Huang, J., et al., "Composite splitting algorithms for convex optimization." Computer Vision and Image Understanding (2011) 115(12): 1610-1622.

Jezzard, P., et al., "Correction for geometrical distortion in echo planar images from bo field variations" Magn Reson Med. (1995) 34:65-73.

Kolmogorov, et al., "What energy functions can be minimized via graph cuts?" IEEE Trans. Pattern Anal. Mach. Intell (2004) 26:147-159.

Mangova, M., et al., "Dynamic magnetic resonance imaging using compressed sensing with multi scale low rank penalty" 40th International Conference on Telecommunications and signal processing (TSP) (2017) pp. 780-783.

Mansfield, P., "Multi-planar image formation using NMR spin-echoes" J Phys C. (1977) 10:L55-L58.

Mengye, L., et al., "Improved Parallel Imaging Reconstruction of EPI using Inversely Distortion Corrected FLASH as Calibration Data" Proceeding in ISMRM 2018. (Abstract#3509).

Newitt, D.C., et al., "Gradient Nonlinearity Correction to Improve Apparent Diffusion Coefficient Accuracy and Standardization in the American College of Radiology Imaging Network 6698 Breast Cancer Trial." J Magn Reson Imaging (2015) 42(4): 908-919.

Sutton, B., et al., "Fast, iterative image reconstruction for MRI in the presence of field inhomogeneities" IEEE Trans Med Imaging (2003) 22: 178-188.

Tao, S., et al., "Integrated Image Reconstruction and Gradient Nonlinearity Correction" Magn Reson Med (2015) 74 (4):1019-1031.

Tao, S., et al., "Gradient Pre-emphasis to Counteract First-Order Concomitant Fields on Asymmetric MRI Gradient Systems" Magn Reson Med. (2017) 77:2250-2262.

Usman, M., et al., "An integrated model-based framework for the correction of signal pile-up and translational offsets in prostate diffusion MRI" Proceeding in ISMRM 2018. (Abstract#1639).

Weavers, P.T., et al., "Technical Note: Compact three-tesla magnetic resonance imager with high-performance gradients passes ACR image quality and acoustic noise tests" Med Phys (2016) 43(3):1259-1264.

Weavers, P.T., et al., "BO concomitant field compensation for MRI systems employing asymmetric transverse gradient coils" Magn Reson Med (2018) 79, 1538-1544.

Yarach, U., et al., "Model-based iterative Reconstruction for Echo Planar Imaging: Methods and Applications" 53rd Asilomar Conference on Signals, Systems, and Computers (2019) IEEE pp. 61-64.

Zahneisen, B., et al., "Extended hybrid-space SENSE for EPI: Off-resonance and eddy current corrected joint interleaved blip-up/down reconstruction" NeuroImage (2017) 153: 97-108.

International Search Report issued for PCT/US2020/029471 dated Jul. 21, 2020.

International Preliminary Report on Patentability issued for PCT/US2020/029471 dated Sep. 28, 2021.

* cited by examiner

MODEL-BASED ITERATIVE RECONSTRUCTION FOR MAGNETIC RESONANCE IMAGING WITH ECHO PLANAR READOUT

CROSS-REFERENCE TO RELATED APPLICATIONS

This application represents the national stage entry of PCT/US2020/029471 filed on Apr. 23, 2020 and claims the benefit of U.S. Provisional Patent Application Ser. No. 62/839,019 on Apr. 26, 2019, and entitled "Model-Based Iterative Reconstruction for Magnetic Resonance Imaging with Echo Planar Readout," the contents of which is herein incorporated by reference in its entirety.

STATEMENT REGARDING FEDERALLY SPONSORED RESEARCH

This invention was made with government support under EB024450 awarded by the National Institutes of Health. The government has certain rights in the invention.

BACKGROUND

Echo planar imaging ("EPI") is widely used clinically for its speed, but is known to be sensitive to hardware non-idealities including $B_0$ field inhomogeneity, eddy-currents, and gradient nonlinearity ("GNL"). Such non-idealities are not typically managed during image reconstruction, resulting in geometrically distorted images. To correct these distortions, image-based post-processing methods (e.g., interpolation) are commonly applied, but these tend to degrade resolution and provide only partial corrections. Hybrid reconstruction models that leverage image-based corrections within an iterative framework have also been proposed, with some success. However, there remains a need for a comprehensive reconstruction framework that prospectively accounts for multiple non-idealities.

SUMMARY OF THE DISCLOSURE

The present disclosure addresses the aforementioned drawbacks by providing a method for reconstructing an image from data acquired with a magnetic resonance imaging (MRI) system. The method includes accessing k-space data with a computer system. The k-space data are acquired from a subject using an MRI system operating an echo planar imaging (EPI) pulse sequence. Signal model parameters are also accessed with the computer system. The signal model parameters are associated with non-idealities of the MRI system used to acquire the k-space data. An image is reconstructed from the k-space data using the computer system to construct a signal model based in part on the signal model parameters and to optimize an objective function that is based on the signal model. The signal model prospectively accounts for non-idealities of the MRI system.

In one configuration, a method is provided for reconstructing an image from data acquired with a magnetic resonance imaging (MRI) system. The steps of the method include accessing k-space data with a computer system. The k-space data are acquired from a subject using an MRI system operating an echo planar imaging (EPI) pulse sequence. The method also includes accessing signal model parameters with the computer system. The signal model parameters are associated with non-idealities of the MRI system used to acquire the k-space data. The method also includes reconstructing an image from the k-space data using the computer system to construct a signal model based in part on the signal model parameters and to optimize an objective function that is based on the signal model, which prospectively accounts for non-idealities of the MRI system.

In some configurations, the non-idealities of the MRI system are associated with off-resonance effects, gradient nonlinearities, and ramp-sampling. The k-space data may be undersampled k-space data, and the k-space data may be acquired using a partial Fourier encoding.

In some configurations, the signal model parameters include coil sensitivity profile data associated with a radio frequency (RF) coil array used when acquiring the k-space data. The coil sensitivity profile data may be accessed from a data storage of the MRI system. The signal model parameters may include ramp-sampling data, which may be accessed from a pulse sequence server of the MRI system. The signal model parameters may include gradient nonlinearity data, main magnetic field (B0) map data, and/or phase reference data. The phase reference data may be generated by optimizing an objective function that is based on the signal model parameters without phase constraints, and reconstructing the image may include updating the signal model using the phase reference data.

In some configurations, the objective function is optimized using a nonlinear regularization. The nonlinear regularization may be a wavelet-based sparsity regularization for improved noise performance. The nonlinear regularization may include use of a set of convolutional linear transform functions for improved noise performance.

In some configurations, the k-space data includes multiple EPI k-space data sets and the method may include simultaneously reconstructing the multiple EPI k-space data sets using a model based iterative reconstruction procedure.

In some configurations, the objective function may be optimized using a nonlinear regularization that includes a regularization functional that considers each k-space data set separately. The objective function may be optimized using a nonlinear regularization that includes a regularization functional that considers two or more of the k-space data sets jointly. The nonlinear regularization may promote a set of reconstructed images to be low-rank. The nonlinear regularization may locally promote low-rankedness at one or more scales.

In some configurations, the pulse sequence implemented with the MRI system to acquire the k-space data is a single-shot EPI pulse sequence. In some configurations, the pulse sequence implemented with the MRI system to acquire the k-space data is a multi-shot EPI pulse sequence.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods that implement a model-based reconstruction that prospectively and simultaneously accounts for multiple non-idealities in accelerated single-shot-EPI acquisitions. In some implementations, non-linear regularization (e.g., sparsity regularization) is also incorporated to mitigate noise amplification. The methods described in the present disclosure provide for images with reduced distortions and noise amplification effects relative to those images that are processed post-reconstruction to correct for non-idealities. For instance, phantom and in vivo experiments have demonstrated that the systems and methods described in the present disclosure improve geometric accuracy and image SNR relative to both online standard reconstructions as well as widely used post-processing strategies.

As noted, the systems and methods described in the present disclosure implement an image reconstruction from data acquired using an EPI acquisition, such as a single-shot EPI acquisition. The signal model for this acquisition can be described as follows.

Let TE, $\Delta t$, and T denote the echo time, dwell time, and echo-spacing times of a single-shot EPI acquisition. Neglecting $T_2^*$ and presuming pre-correction of eddy-current and gradient delay effects, the signal measured during readout $m \in [0, M)$ of phase-encoding line $n \in [0, N)$ can be modeled as:

$$g_c[m,n] = \int_{\Omega_x} \int_{\Omega_y} s_c(x,y) f(x,y) e^{-j\Delta\omega_0(x,y)\tau[m,n]} \quad (1)$$
$$e^{-j((-1)^n k_x[m]\eta_x(x,y) + k_y[n]\eta_y(x,y))} dx\, dy + \varepsilon[m,n];$$

where f is the target signal, $k_x$ and $k_y$ are sampling maps, $s_c$ is the sensitivity profile for coil $c \in [0, C)$, $\omega_0$ is the $B_0$-field map, $$\tau[m,n] = TE + \left(m - \frac{M-1}{2}\right)\Delta t + \left(n - \frac{N-1}{2}\right)T$$

denotes sampling-time, $\eta_x(x, y)$ and $\eta_y(x, y)$ are gradient nonlinearity ("GNL") maps, and $\varepsilon$ is Gaussian noise. Note that Eqn. (1) accommodates ramp-sampling, parallel imaging, and partial Fourier acceleration.

Because EPI uses high readout-bandwidth, $\Delta t \ll T$, and off-resonances are primarily manifest along the phase encoded (i.e., blipped) direction, $\Delta t \approx 0$ can be assumed. Letting, $$u(x,y) = f(x,y) e^{j\Delta\omega_0(x,y)TE}$$

and time-segmenting Eqn. (1) yields:

$$g_c[m,n] = \sum_{l=0}^{L} \Phi_l(n) \Big\{ s_c[p,q] u[p,q] e^{-j\Delta\omega_0[p,q][\gamma_l - \frac{N-1}{2}]T} \quad (2)$$
$$e^{-j((-1)^n k_x[m]\eta_p[p,q] + k_y[n]\eta_q[p,q])} \Big\} + \varepsilon[m,n];$$

Where $\Phi_l$ is a spectral window, $\gamma_l$ denotes the center of segment l, and $p \in [0, P)$ and $q \in [0, Q)$ are pixel indices. Defining, $$W_l = \text{diag}\left\{e^{-j\Delta\omega_0[p,q][\gamma_l - \frac{N-1}{2}]T}\right\}$$

and $$S = [\text{diag}\{s_0\} \ldots \text{diag}\{s_{C-1}\}]^T$$

Eqn. (2) abstracts to:

$$g = \left(I \otimes \sum_{l=0}^{L} \Phi_l FW_l\right) Su + \varepsilon = Au + \varepsilon; \quad (3)$$

where F is a Fourier transform. If a phase reference, $\theta$, for u is available, the complex target reduces to, $$u = \text{diag}\{e^{j\theta}\} v = P(\theta) v$$

where $v \in \mathbb{T}^{12}$.

The target image in Eqn. (2) can be estimated, as one non-limiting example, via regularized least squares estimation:

$$\min_{v \in \mathbb{C}} \{J(v) \Box \beta R(v) + \|AP(\theta)v - g\|_2^2\}; \quad (4)$$

where $\beta > 0$ is a regularization parameter. As one non-limiting example, a joint redundant wavelet sparsity regularization, such as the following, can be used:

$$R(v) = \left\| \sum_{k \in \xi} (\delta_k^T \otimes \Psi \Gamma_k v) \right\|_{1,2}; \quad (5)$$

where $\delta$ and $\otimes$ are Kronecker's delta and product, $\Psi$ is the Daubechies-4-wavelet, $\Gamma_k$ is a shift operator over neighborhood $\xi$, and $\|\cdot\|_{1,2}$ is the matrix-1,2 norm. Because Eqn. (4) is convex, it can be solved using techniques such as FISTA with composite splitting. For efficiency, the Fourier transform can be implemented as a type-III non-uniform fast Fourier transform ("NUFFT").

Figure 1:
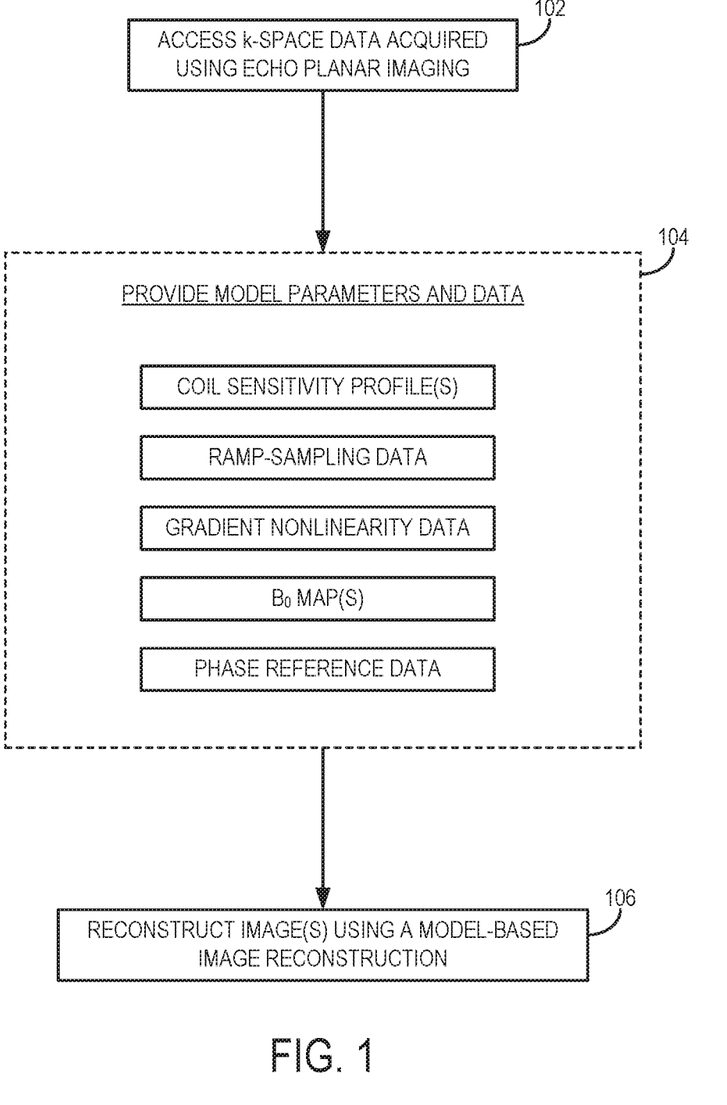
FIG. 1 is a flowchart setting forth the steps of an example method for reconstructing images from k-space data acquired using an EPI acquisition and using a comprehensive model-based image reconstruction.

Referring now to FIG. 1, a flowchart is illustrated as setting forth the steps of a non-limiting example of a method for reconstructing an image from magnetic resonance data (e.g., k-space data) using a comprehensive model-based image reconstruction, such as those described above in detail. The method begins by accessing k-space data for reconstruction, as indicated at step 102. Accessing the k-space data can include retrieving previously acquired data from a memory or other data storage device or medium. Additionally or alternatively, accessing the k-space data can include acquiring such data with an MRI system and communicating that data to the computer system, which may be a part of the MRI system. As described above, the k-space data are generally acquired using an EPI pulse sequence, such as a single-shot EPI pulse sequence, whether or not undersampling is also implemented. As another example, data can be acquired using a multi-shot EPI pulse sequence.

As part of the model-based integrated reconstruction process, various parameters and data are provided to the computer system in order to implement or otherwise establish the model used for reconstruction, as generally depicted by process block 104. As noted above, these parameters or data include coil sensitivity profiles, ramp-sampling data or information, GNL data or information, $B_0$ maps, and phase reference data or information.

In some implementations the coil sensitivity profiles can be vendor-provided coil sensitivity profiles. In some other implementations, the coil sensitivity profiles can be estimated or otherwise measured using any suitable technique known to those skilled in the magnetic resonance imaging arts.

As an example, ramp-sampling data can be provided from the pulse sequence server of the MRI system. The GNL information can be provided, as non-limiting examples, by retrieving the appropriate information from the MRI system data storage, by performing an appropriate electromagnetic simulation, or by using a calibration procedure based on phantom images acquired with the MRI system.

The $B_0$ field maps can be estimated using any suitable $B_0$ mapping techniques. As one non-limiting example, the $B_0$ maps can be estimated from a calibration scan (e.g., a dual-echo GRE calibration scan). For instance, the $B_0$ maps can be estimated from such a calibration scan using a graph cut-based procedure. As one non-limiting example, the phase reference, $\theta$, can be obtained by minimizing Eqn. (4) without phase constraints.

Images are then reconstructed using a model-based image reconstruction, such as those described above, as indicated at step 106. The model-based image reconstruction can be implemented by constructing a comprehensive signal model that incorporates the model parameters and data provided in step 104, or otherwise accessing a previously constructed comprehensive signal model and incorporating the model parameters and data provided in step 104. For instance, images are reconstructed using a model-based estimation process that provides correction for multiple different non-idealities during, rather than after, image reconstruction. In general, this process is based on a comprehensive signal model that incorporates the aforementioned model parameters and data, such as the signal models referenced in Eqns. (1), (2), or (3).

As an example, the image reconstruction can be implemented by solving the minimization problem in Eqn. (4). As described above, this reconstruction problem can be regularized using a nonlinear regularization, such as the sparsity regularization described with respect to Eqn. (5). In other implementations, the nonlinear regularization can include the use of a set of convolutional linear transform functions for improved noise performance.

In some instances, the acquired data include a plurality of k-space data sets that can be simultaneously reconstructed using the model-based image reconstruction. In these instances, the nonlinear regularization can include a regularization functional that considers each k-space data set separately. Alternatively, the regularization function can consider two or more of the k-space data sets jointly. The nonlinear regularization may also promote the reconstructed image set to be low-rank. In some instances, the low-rankedness can be promoted locally at one or more scales.

In one non-limiting example study, two healthy volunteers were imaged using a compact 3T MRI system: (G=80 mT/m, SR=700 T/m/s), with C=32 or C=8 head-only receiver-only RF head coils. Following field map, coil sensitivity, and eddy current calibration, single-shot EPI acquisitions were performed with the following parameters: FOV=220×200 mm$^2$, SENSE R=2, Partial Fourier=5/8, TR/TE=3700/50 ms, and BW=250 kHz. Prior to MBIR, eddy current correction was performed in k-space using vendor-provided tools. MBIR was performed in Matlab, using a 2X-oversampled NUFFT with width=5 Kaiser-Bessel kernel, L=N time segments, and a 7×7 shift window. FISTA was executed for 30 iterations. The regularization parameter was chosen manually ($\beta$=0.02). For comparison, vendor reconstructions were saved and post-processed using standard intensity corrected image interpolation for distortion correction.

The distortion correction performance of the proposed MBIR strategy was tested against the vendor reconstruction, with and without post-processing. Both conventional post-processing and MBIR effectively corrected coarse distortion, with the latter providing modest improvements; however, MBIR offered reduced noise amplification relative to both the original and post-processed vendor reconstructions. This advantage was particularly apparent in low-contrast structures like the caudate head.

Systems and methods for a comprehensive MBIR strategy for single-shot EPI that prospectively accounts for off-resonance, GNL, ramp-sampling, and parallel imaging and partial Fourier-type acceleration have been provided. In some implementations, the MBIR strategy leverages wavelet-based sparsity regularization for improved noise performance. The proposed framework could benefit any EPI-based application, such as diffusion or elastography.

Figure 2:
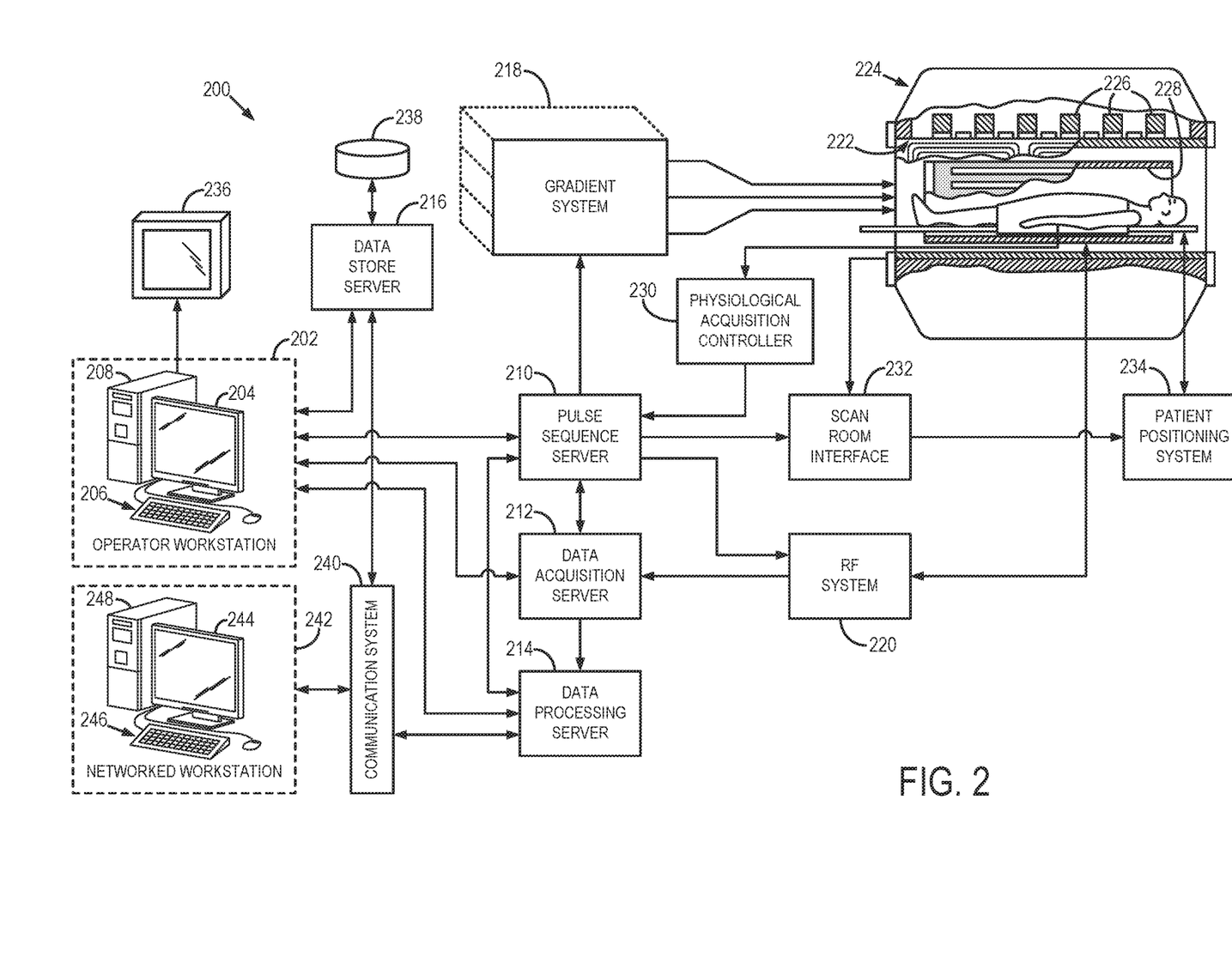
FIG. 2 is a block diagram of an example MRI system that can implement the systems and methods described in the present disclosure.

Referring now to FIG. 2, a non-limiting example of an MRI system 200 that can implement the methods described herein is illustrated. The MRI system 200 includes an operator workstation 202 that may include a display 204, one or more input devices 206 (e.g., a keyboard, a mouse), and a processor 208. The processor 208 may include a commercially available programmable machine running a commercially available operating system. The operator workstation 202 provides an operator interface that facilitates entering scan parameters into the MRI system 200. The operator workstation 202 may be coupled to different servers, including, for example, a pulse sequence server 210, a data acquisition server 212, a data processing server 214, and a data store server 216. The operator workstation 202 and the servers 210, 212, 214, and 216 may be connected via a communication system 240, which may include wired or wireless network connections.

The pulse sequence server 210 functions in response to instructions provided by the operator workstation 202 to operate a gradient system 218 and a radiofrequency ("RF") system 220. Gradient waveforms for performing a prescribed scan are produced and applied to the gradient system 218, which then excites gradient coils in an assembly 222 to produce the magnetic field gradients $G_x$, $G_y$, and $G_z$ that are used for spatially encoding magnetic resonance signals. The gradient coil assembly 222 forms part of a magnet assembly 224 that includes a polarizing magnet 226 and a whole-body RF coil 228.

RF waveforms are applied by the RF system 220 to the RF coil 228, or a separate local coil to perform the prescribed magnetic resonance pulse sequence. Responsive magnetic resonance signals detected by the RF coil 228, or a separate local coil, are received by the RF system 220. The responsive magnetic resonance signals may be amplified, demodulated, filtered, and digitized under direction of commands produced by the pulse sequence server 210. The RF system 220 includes an RF transmitter for producing a wide variety of RF pulses used in MRI pulse sequences. The RF transmitter is responsive to the prescribed scan and direction from the pulse sequence server 210 to produce RF pulses of the desired frequency, phase, and pulse amplitude waveform. The generated RF pulses may be applied to the whole-body RF coil 228 or to one or more local coils or coil arrays.

The RF system 220 also includes one or more RF receiver channels. An RF receiver channel includes an RF preamplifier that amplifies the magnetic resonance signal received by the coil 228 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \qquad (6);$$

and the phase of the received magnetic resonance signal may also be determined according to the following relationship:

$$\varphi = \tan^{-1}\left(\frac{Q}{I}\right). \qquad (7)$$

The pulse sequence server 210 may receive patient data from a physiological acquisition controller 230. By way of example, the physiological acquisition controller 230 may receive signals from a number of different sensors connected to the patient, including electrocardiograph ("ECG") signals from electrodes, or respiratory signals from a respiratory bellows or other respiratory monitoring devices. These signals may be used by the pulse sequence server 210 to synchronize, or "gate," the performance of the scan with the subject's heart beat or respiration.

The pulse sequence server 210 may also connect to a scan room interface circuit 232 that receives signals from various sensors associated with the condition of the patient and the magnet system. Through the scan room interface circuit 232, a patient positioning system 234 can receive commands to move the patient to desired positions during the scan.

The digitized magnetic resonance signal samples produced by the RF system 220 are received by the data acquisition server 212. The data acquisition server 212 operates in response to instructions downloaded from the operator workstation 202 to receive the real-time magnetic resonance data and provide buffer storage, so that data is not lost by data overrun. In some scans, the data acquisition server 212 passes the acquired magnetic resonance data to the data processor server 214. In scans that require information derived from acquired magnetic resonance data to control the further performance of the scan, the data acquisition server 212 may be programmed to produce such information and convey it to the pulse sequence server 210. For example, during pre-scans, magnetic resonance data may be acquired and used to calibrate the pulse sequence performed by the pulse sequence server 210. As another example, navigator signals may be acquired and used to adjust the operating parameters of the RF system 220 or the gradient system 218, or to control the view order in which k-space is sampled. In still another example, the data acquisition server 212 may also process magnetic resonance signals used to detect the arrival of a contrast agent in a magnetic resonance angiography ("MRA") scan. For example, the data acquisition server 212 may acquire magnetic resonance data and processes it in real-time to produce information that is used to control the scan.

The data processing server 214 receives magnetic resonance data from the data acquisition server 212 and processes the magnetic resonance data in accordance with instructions provided by the operator workstation 202. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 214 are conveyed back to the operator workstation 202 for storage. Real-time images may be stored in a data base memory cache, from which they may be output to operator display 202 or a display 236. Batch mode images or selected real time images may be stored in a host database on disc storage 238. When such images have been reconstructed and transferred to storage, the data processing server 214 may notify the data store server 216 on the operator workstation 202. The operator workstation 202 may be used by an operator to archive the images, produce films, or send the images via a network to other facilities.

The MRI system 200 may also include one or more networked workstations 242. For example, a networked workstation 242 may include a display 244, one or more input devices 246 (e.g., a keyboard, a mouse), and a processor 248. The networked workstation 242 may be located within the same facility as the operator workstation 202, or in a different facility, such as a different healthcare institution or clinic.

The networked workstation 242 may gain remote access to the data processing server 214 or data store server 216 via the communication system 240. Accordingly, multiple networked workstations 242 may have access to the data processing server 214 and the data store server 216. In this manner, magnetic resonance data, reconstructed images, or other data may be exchanged between the data processing server 214 or the data store server 216 and the networked workstations 242, such that the data or images may be remotely processed by a networked workstation 242.

Figure 3:
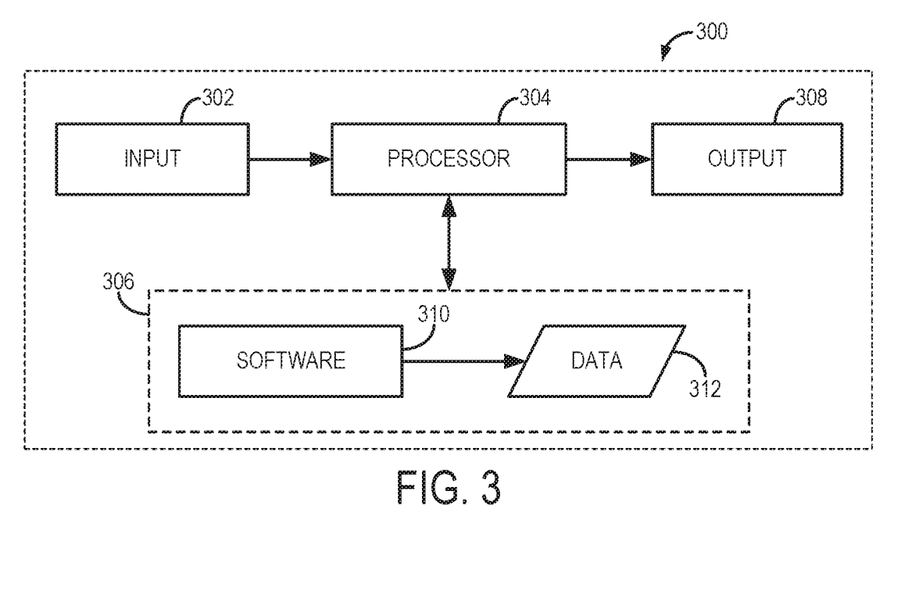
FIG. 3 is a block diagram of an example computer system that can implement the systems and methods described in the present disclosure.

Referring now to FIG. 3, a block diagram of a non-limiting example of a computer system 300 that can perform the methods described in the present disclosure is shown. The computer system 300 generally includes an input 302, at least one hardware processor 304, a memory 306, and an output 308. Thus, the computer system 300 is generally implemented with a hardware processor 304 and a memory 306.

In some embodiments, the computer system 300 can be a workstation, a notebook computer, a tablet device, a mobile device, a multimedia device, a network server, a mainframe, one or more controllers, one or more microcontrollers, or any other general-purpose or application-specific computing device.

The computer system 300 may operate autonomously or semi-autonomously, or may read executable software instructions from the memory 306 or a computer-readable medium (e.g., a hard drive, a CD-ROM, flash memory), or may receive instructions via the input 302 from a user, or any another source logically connected to a computer or device, such as another networked computer or server. Thus, in some embodiments, the computer system 300 can also include any suitable device for reading computer-readable storage media.

In general, the computer system 300 is programmed or otherwise configured to implement the methods and algorithms described in the present disclosure. For instance, the computer system 300 can be programmed to implement image reconstruction algorithms, such as those described in the present disclosure.

The input 302 may take any suitable shape or form, as desired, for operation of the computer system 300, including the ability for selecting, entering, or otherwise specifying parameters consistent with performing tasks, processing data, or operating the computer system 300. In some aspects, the input 302 may be configured to receive data, such as data acquired with an MRI system. Such data may be processed as described above to reconstruct images. In addition, the input 302 may also be configured to receive any other data or information considered useful for reconstructing images using the methods described above.

Among the processing tasks for operating the computer system 300, the one or more hardware processors 304 may also be configured to carry out any number of post-processing steps on data received by way of the input 302.

The memory 306 may contain software 310 and data 312, such as data acquired with an MRI system, and may be configured for storage and retrieval of processed information, instructions, and data to be processed by the one or more hardware processors 304. In some aspects, the software 310 may contain instructions directed to implementing image reconstruction algorithms, such as those described in the present disclosure.

In addition, the output 308 may take any shape or form, as desired, and may be configured for displaying reconstructed images, in addition to other desired information.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for reconstructing an image from data acquired with a magnetic resonance imaging (MRI) system, the steps of the method comprising:
   (a) accessing k-space data with a computer system, wherein the k-space data are acquired from a subject using an MRI system operating an echo planar imaging (EPI) pulse sequence;
   (b) accessing signal model parameters with the computer system, wherein the signal model parameters are associated with non-idealities of the MRI system used to acquire the k-space data; and
   (c) reconstructing an image from the k-space data while compensating for the non-idealities using the computer system to construct a single signal model based in part on the signal model parameters and to optimize an objective function that is based on the signal model, wherein the single signal model prospectively accounts for non-idealities of the MRI system such that the non-idealities are compensated for while the image is being reconstructed using the single signal model.

2. The method as recited in claim 1, wherein the non-idealities of the MRI system are associated with off-resonance effects, gradient nonlinearities, and ramp-sampling.

3. The method as recited in claim 2, wherein the k-space data are undersampled k-space data.

4. The method as recited in claim 3, wherein the k-space data are acquired using a partial Fourier encoding.

5. The method as recited in claim 1, wherein the signal model parameters comprise coil sensitivity profile data associated with a radio frequency (RF) coil array used when acquiring the k-space data.

6. The method as recited in claim 5, wherein the coil sensitivity profile data are accessed from a data storage of the MRI system.

7. The method as recited in claim 1, wherein the signal model parameters comprise ramp-sampling data.

8. The method as recited in claim 7, wherein the ramp-sampling data are accessed from a pulse sequence server of the MRI system.

9. The method as recited in claim 1, wherein the signal model parameters comprise gradient nonlinearity data.

10. The method as recited in claim 1, wherein the signal model parameters comprise main magnetic field ($B_0$) map data.

11. The method as recited in claim 1, wherein the signal model parameters comprise phase reference data.

12. The method as recited in claim 11, wherein the phase reference data are generated by optimizing the objective function that is based on the signal model parameters without phase constraints, and wherein reconstructing the image includes updating the signal model using the phase reference data.

13. The method as recited in claim 1, wherein the objective function is optimized using a nonlinear regularization.

14. The method as recited in claim 13, wherein the nonlinear regularization is a wavelet-based sparsity regularization for improved noise performance.

15. The method as recited in claim 13, wherein the nonlinear regularization includes use of a set of convolutional linear transform functions for improved noise performance.

16. The method as recited in claim 1, wherein the k-space data comprise multiple EPI k-space data sets and step (c) includes simultaneously reconstructing the multiple EPI k-space data sets using a model based iterative reconstruction procedure.

17. The method as recited in claim 16, wherein the objective function is optimized using a nonlinear regularization that includes a regularization functional that considers each k-space data set separately.

18. The method as recited in claim 16, wherein the objective function is optimized using a nonlinear regularization that includes a regularization functional that considers two or more of the k-space data sets jointly.

19. The method as recited in claim 18, wherein the nonlinear regularization promotes a set of reconstructed images to be low-rank.

20. The method as recited in claim 19, wherein the nonlinear regularization locally promotes low-rankedness at one or more scales.

21. The method as recited in claim 1, wherein the pulse sequence implemented with the MRI system to acquire the k-space data is a single-shot EPI pulse sequence.

22. The method as recited in claim 1, wherein the pulse sequence implemented with the MRI system to acquire the k-space data is a multi-shot EPI pulse sequence.

* * * * *

UNITED STATES PATENT AND TRADEMARK OFFICE
CERTIFICATE OF CORRECTION

PATENT NO. : 12,085,631 B2  
APPLICATION NO. : 17/606645  
DATED : September 10, 2024  
INVENTOR(S) : Joshua D. Trzasko et al.

Page 1 of 1

It is certified that error appears in the above-identified patent and that said Letters Patent is hereby corrected as shown below:

On the Title Page

Item (73) Assignee, "May" should be --Mayo--.

In the Specification

Column 3, Line 52, "$\Delta t \!\perp\! T$" should be --$\Delta t \ll T$--.

Column 4, Line 24, "$v \in \mathbb{I}^{12}$" should be --$v \in \mathbb{R}^{12}$--.

Column 4, Line 30, Eq. (4), "$\min_{v \in \square}\{J(v) \square \beta R(v) + \|AP(\theta)v - g\|_2^2\}$" should be --$\min_{v \in \mathbb{R}}\{J(v) \triangleq \beta R(v) + \|AP(\theta)v - g\|_2^2\}$--.

Signed and Sealed this  
Fifteenth Day of April, 2025

Coke Morgan Stewart  
*Acting Director of the United States Patent and Trademark Office*